US009161740B2

(12) United States Patent
Harhen

(10) Patent No.: US 9,161,740 B2
(45) Date of Patent: *Oct. 20, 2015

(54) PROBE WITH AN ADAPTIVE BENDING SECTION

(76) Inventor: Edward Paul Harhen, Duxbury, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/437,561

(22) Filed: Apr. 2, 2012

(65) Prior Publication Data

US 2012/0190988 A1     Jul. 26, 2012

Related U.S. Application Data

(60) Division of application No. 12/267,860, filed on Nov. 10, 2008, now Pat. No. 8,172,758, which is a continuation-in-part of application No. 11/681,837, filed on Mar. 5, 2007.

(60) Provisional application No. 60/987,080, filed on Nov. 11, 2007, provisional application No. 60/886,471, filed on Jan. 24, 2007, provisional application No. 60/779,626, filed on Mar. 6, 2006.

(51) Int. Cl.
| | |
|---|---|
| *A61B 8/12* | (2006.01) |
| *A61B 8/00* | (2006.01) |
| *A61B 1/005* | (2006.01) |
| *A61B 5/03* | (2006.01) |
| *A61B 5/01* | (2006.01) |

(Continued)

(52) U.S. Cl.
CPC .............. *A61B 8/445* (2013.01); *A61B 1/0051* (2013.01); *A61B 8/12* (2013.01); *A61B 1/00071* (2013.01); *A61B 5/01* (2013.01); *A61B 5/03* (2013.01)

(58) Field of Classification Search
CPC ............ A61B 8/12; A61B 8/445; A61B 5/01; A61B 5/03; A61B 5/0051; A61B 1/00071
See application file for complete search history.

(56) References Cited

U.S. PATENT DOCUMENTS 5,105,819 A * 4/1992 Wollschlager et al. ....... 600/463
5,271,381 A * 12/1993 Ailinger et al. ............... 600/128

(Continued)

FOREIGN PATENT DOCUMENTS

| GB | 191303531 | 7/1913 |
| WO | 02/069806 A2 | 9/2002 |

OTHER PUBLICATIONS

Search Report and Written Opinion from related application PCT/US2007/063314, Mailed Nov. 16, 2007, 13 pages.

(Continued)

*Primary Examiner* — Long V Le
*Assistant Examiner* — Angela M Hoffa

(57) ABSTRACT

When transesophageal echocardiography is used to obtain a transgastric short axis view of the left ventricle of the heart, the best place to position the transducer is in the fundus of the stomach, aimed up through the left ventricle. The probes disclosed herein facilitate placement of the transducer in the optimum position within the fundus, despite wide variations in the distance between the lower esophageal sphincter and the fundus among different subjects. In one preferred embodiment, the ultrasound probe uses a bending section with a series of vertebrae and stiffening that is more flexible proximally and less flexible distally, which causes the probe to bend relatively sharply at the point where the probe exits the lower esophageal sphincter. The flexibility of the proximal-most portion of the bending section is preferably greater than or equal to the flexibility of the interface between the bending section and the shaft.

14 Claims, 8 Drawing Sheets

(51) Int. Cl.
*A61B 1/01* (2006.01)
*A61B 1/00* (2006.01)

(56) References Cited

U.S. PATENT DOCUMENTS

| | | | |
|---|---|---|---|
| 5,295,486 A * | 3/1994 | Wollschlager et al. | 600/447 |
| 5,413,107 A * | 5/1995 | Oakley et al. | 600/463 |
| 5,448,989 A * | 9/1995 | Heckele | 600/142 |
| 5,588,432 A * | 12/1996 | Crowley | 600/439 |
| 5,704,898 A * | 1/1998 | Kokish | 600/141 |
| 5,741,429 A * | 4/1998 | Donadio et al. | 216/8 |
| 5,840,031 A * | 11/1998 | Crowley | 600/440 |
| 5,873,817 A * | 2/1999 | Kokish et al. | 600/143 |
| 5,931,811 A | 8/1999 | Haissaguerre et al. | |
| 6,004,269 A * | 12/1999 | Crowley et al. | 600/439 |
| 6,113,557 A | 9/2000 | Fagan et al. | |
| 6,142,941 A * | 11/2000 | Benhalima et al. | 600/439 |
| 6,183,420 B1 | 2/2001 | Douk et al. | |
| 6,585,717 B1 | 7/2003 | Wittenberger et al. | |
| 6,607,505 B1 | 8/2003 | Thompson et al. | |
| 6,711,428 B2 | 3/2004 | Fuimaono et al. | |
| 6,733,457 B2 * | 5/2004 | Flesch et al. | 600/459 |
| 6,733,499 B2 | 5/2004 | Scheib | |
| 6,804,545 B2 | 10/2004 | Fuimaono et al. | |
| 6,845,257 B2 | 1/2005 | Fuimaono et al. | |
| 6,866,635 B2 * | 3/2005 | Flesch et al. | 600/459 |
| 6,973,339 B2 | 12/2005 | Govari | |
| 6,987,996 B2 | 1/2006 | Fuimaono et al. | |
| 7,011,655 B2 | 3/2006 | Thompson et al. | |
| 7,063,682 B1 | 6/2006 | Whayne et al. | |
| 7,099,711 B2 | 8/2006 | Fuimaono et al. | |
| 7,101,361 B2 * | 9/2006 | Gardeski | 604/523 |
| 7,250,049 B2 | 7/2007 | Roop et al. | |
| 7,371,232 B2 | 5/2008 | Scheib | |
| 7,570,982 B2 | 8/2009 | Fuimaono et al. | |
| 7,610,073 B2 | 10/2009 | Fuimaono et al. | |
| 7,658,723 B2 * | 2/2010 | Von Oepen et al. | 604/103.09 |
| 7,785,318 B2 * | 8/2010 | Von Oepen et al. | 604/525 |
| 7,815,627 B2 * | 10/2010 | Von Oepen et al. | 604/525 |
| 7,853,302 B2 | 12/2010 | Rodriguez et al. | |
| 7,917,187 B2 | 3/2011 | Fuimaono et al. | |
| 8,000,765 B2 | 8/2011 | Rodriguez et al. | |
| 8,007,495 B2 | 8/2011 | McDaniel et al. | |
| 8,172,758 B2 * | 5/2012 | Harhen | 600/459 |
| 2003/0028107 A1 | 2/2003 | Miller et al. | |
| 2004/0068183 A1 | 4/2004 | Knowles | |
| 2005/0059861 A1 | 3/2005 | Nishiie | |
| 2005/0215942 A1 | 9/2005 | Abrahamson et al. | |
| 2006/0135961 A1 * | 6/2006 | Rosenman et al. | 606/108 |
| 2007/0239022 A1 * | 10/2007 | Harhen | 600/459 |
| 2008/0132933 A1 | 6/2008 | Gerber | |
| 2008/0188928 A1 | 8/2008 | Salahieh et al. | |
| 2009/0118621 A1 * | 5/2009 | Harhen | 600/466 |

OTHER PUBLICATIONS

Search Report and Written Opinion from corresponding application PCT/US2008/082980, Mailed Feb. 11, 2009, 13 pages.

* cited by examiner

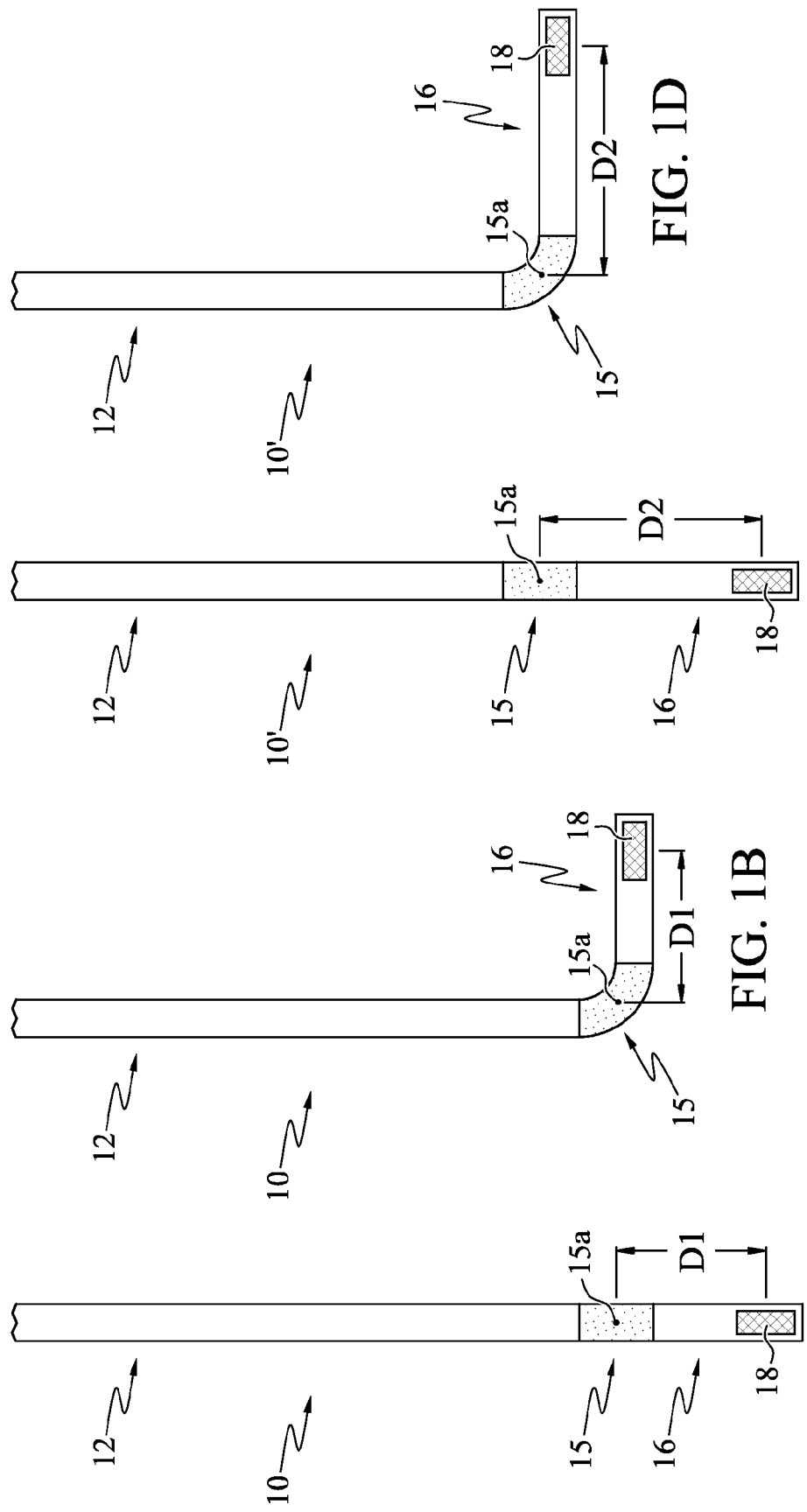

PROBE WITH AN ADAPTIVE BENDING SECTION

CROSS REFERENCE TO RELATED APPLICATIONS

This application is a divisional of U.S. patent application Ser. No. 12/267,860, filed Nov. 10, 2008, which (a) claims the benefit of U.S. Provisional Application 60/987,080, filed Nov. 11, 2007; and (b) is a continuation-in-part of U.S. patent application Ser. No. 11/681,837, filed Mar. 5, 2007, which claims the benefit of U.S. Provisional Application 60/886,471, filed Jan. 24, 2007, and U.S. Provisional Application 60/779,626, filed Mar. 6, 2006. Each of those applications is incorporated herein by reference.

BACKGROUND

Transesophageal echocardiography (TEE) is an ultrasound imaging technique that provides images of the heart for diagnostic and/or monitoring purposes. One particularly beneficial use of TEE is for obtaining images of the transgastric short axis view (TGSAV) of the left ventricle. To obtain the best images of the TGSAV using TEE, the ultrasound transducer should ideally be positioned in the fundus of the stomach, with the ultrasound beam aimed through the left ventricle.

TEE probes for imaging the TGSAV typically contain mechanical articulation mechanisms to bend the distal end the probe into the desired position in the fundus. Since conventional TEE probes are relatively large (i.e., on the order of ½ inch in diameter), the articulation mechanisms can be relatively strong. As a result, when the probe is not perfectly aligned with the desired position, the probe can exert significant forces on the relevant anatomical structures to push the distal end of the probe into the desired location for obtaining the TGSAV. However, when smaller TEE probes are used (e.g., the 5 or 6 mm diameter probes described in U.S. patent application Ser. No. 10/996,816), the probe may not be able to exert enough force to push the distal end of the probe into the desired location.

U.S. application Ser. No. 10/996,816, incorporated herein by reference, discloses a TEE probe for use in adults that is preferably less than 7.5 mm in diameter, more preferably less than 6 mm in diameter, and most preferably about 5 mm in diameter. It also discloses a pediatric TEE probe that is preferably between about 2.5 and 4 mm in diameter.

To obtain the best images of the TGSAV, the ultrasound transducer (which is located in the distal end of the probe) should be positioned in the fundus of the stomach, pressed up against the mucosa. The optimal position of the transducer within the fundus depends on a number of parameters including the size of the heart and the position of the heart relative to the fundus. These parameters may vary, for example, with body size, body habitus, and/or anatomical relationships. The optimum position for the transducer within the fundus is referred to hereinafter as "OPF".

To get the transducer at or near the OPF to perform imaging, the distal end of the probe is inserted in its unbent position into the patient's nose or mouth, down through the patient's esophagus, and into the fundus of the stomach. After the tip of the probe has been inserted to the appropriate depth, the operator (e.g., a doctor) actuates an articulation mechanism to bend the distal end of the probe until it comes into contact with the mucosa lining the superior portion of the fundus, preferably positioning the distal end of the probe at an acceptable position or, most preferably, at the OPF. Once the distal end of the probe is at a position, ultrasound images can be obtained. If, based on the images, it is determined that the distal end is not at an acceptable position or the OPF, the position of the probe may be adjusted to improve the images.

The entrance from the esophagus to the stomach is called the lower esophageal sphincter. The lower esophageal sphincter is a relatively stable area because the esophagus itself has a thicker musculature at this point and because the area is supported where it passes through the diaphragm. If the distance from the lower esophageal sphincter to the OPF was the same in all patients, a probe could be designed with its bending joint located at a corresponding distance from the distal tip of the probe. In practice, however, the distance between the lower esophageal sphincter and the OPF (referred to hereinafter as "LOD") varies from patient to patient. For example, the LOD may typically be between 4-10 cm in adults, and 2-5 cm in children, depending upon body size, body habitus and the position of the heart relative to the diaphragm.

Conventional large TEE probes (e.g., ½ inch in diameter) have a bending point that is located at a fixed distance from the distal tip of the probe, and can exert significant forces on the relevant anatomical structures to push the distal end of the probe into a suitable location for obtaining the TGSAV. However, the operator of the device may not perceive the forces as being high due to the mechanical advantage provided by the articulation controls. The distal tip positioning of conventional probes is accomplished by deflecting the relatively compliant lower esophagus and upper stomach cavity with a stiff probe insertion tube and by a powerful bending section within the probe. However, when smaller TEE probes are used, the probe will often be unable to exert enough force to push the distal end of the probe into a suitable location. Examples of smaller TEE probes include TEE probes for adults that are less than 7.5 mm in diameter, and pediatric TEE probes that are preferably less than 4 mm in diameter (as described in U.S. application Ser. No. 10/996,816).

BRIEF SUMMARY OF THE INVENTION

A probe is provided with a transducer disposed in the distal section, a bending section disposed proximal to the transducer, and a shaft disposed proximal to the bending section. The proximal portion of the bending section is more flexible than the distal portion of the bending section and the flexibility of the proximal-most portion of the bending section is greater than or equal to the flexibility of the interface between the bending section and the shaft. This arrangement causes the bending section to conform to the relevant anatomy by first bending near the proximal portion of the bending section, or by bending a greater amount in the proximal portion as compared to the distal portion of the bending section.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIGS. 1A and 1B illustrate the distal portion of an ultrasound probe in its straight and bent positions, respectively.

FIGS. 1C and 1D illustrate the distal portion of another ultrasound probe that has a different bending point (in its straight and bent positions, respectively).

DESCRIPTION OF THE PREFERRED EMBODIMENTS

Figure 2C:
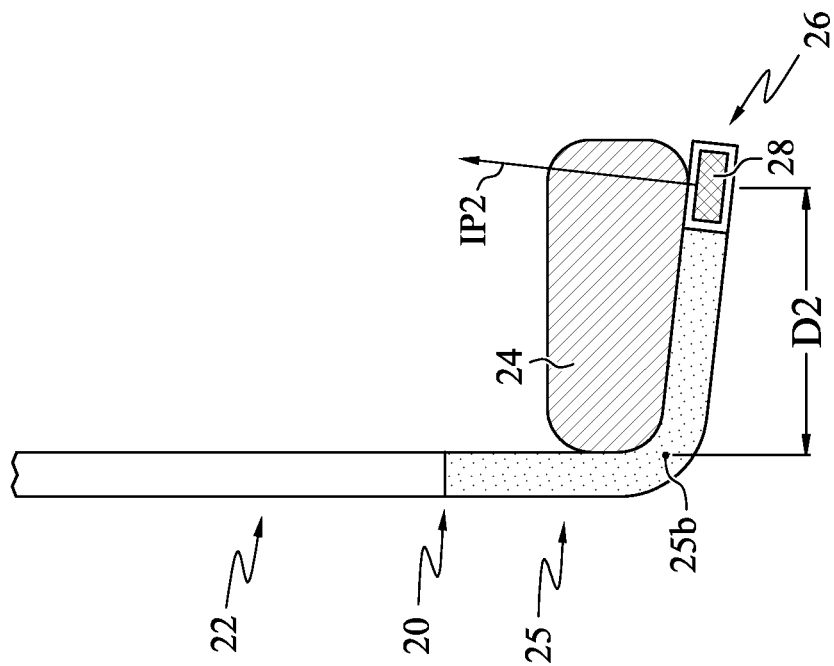
FIGS. 2A, 2B, and 2C illustrate the distal portion of another embodiment of an ultrasound probe that is configured to bend in different locations depending on the anatomy of the patient.

FIGS. 1A-1D illustrate a system for positioning a transducer in a desired anatomical location (e.g., in the OPF, aimed to image the TGSAV of the left ventricle) that can be used even with smaller probes. In this embodiment, a set of probes is provided as a kit (not shown), with each probe in the kit designed to bend at a different point along the proximal-distal longitudinal axis of the probe. When using the system for ultrasound imaging, the operator selects one of the probes from the kit (i.e., the one that is expected to fit best), and uses that probe to obtain the desired images. Note that while only two probes from the kit are illustrated in FIGS. 1A-1D, the kit preferably includes additional probes (not shown) to cover all the bending points that may be needed. For example, a kit may include five probes, with their bending points located 4, 5, 6, 7, and 8 cm from the transducer, respectively.

FIGS. 1A and 1B illustrate a first probe 10 from the kit in straight and bent positions, respectively. FIGS. 1C and 1D similarly illustrate a second probe 10' from the kit in straight and bent positions, respectively. The first probe 10 and second probe 10' each include a flexible shaft 12, which is preferably stiff enough yet flexible enough to permit the operator to position the distal ends 16 of the first probe 10 or second probe 10' into the relevant anatomical structures (e.g., the esophagus) at the desired depth of penetration. The shaft 12 is preferably flexible enough and thin enough to permit placement of the probe within the relevant anatomy, and to permit the shaft to be left in-situ for extended periods of time without causing problems or excessive discomfort. Examples of suitable configurations for the shaft include those found in conventional nasogastric and feeding tubes, as well as transesophageal Doppler monitoring probes such as those made by Deltex Medical Group plc of Chichester, United kingdom. Optionally, the shaft 12 may be designed with a pair of counterwound metal helixes, with one wound clockwise and one wound counterclockwise, which provides crush resistance, kink resistance, and torquability. Simpler shafts may also be used, e.g., a teflon sleeve surrounded by a metal braid that is surrounded by a urethane outer shell. The crush resistance, kink resistance, and torquability of such simpler shafts may be improved by filling some or all of the empty space within the shaft with any suitable material such as one or more concentric tubes. The empty space may even be filled with water, another suitable liquid, or a suitable gel.

The components that are proximal to the flexible shaft 12 (such as a handle with articulation controls, an interface cable, and a connector that mates to an imaging system) are well known to persons skilled in the relevant arts, and as such are not described in detail herein. Similarly, the mechanism for transmitting the operator's actuations of the controls through the shaft to the working end of the probe (e.g., pull wires, not shown) are also well known and not described herein.

Distally beyond the flexible shaft 12 is a bending section 15 that is much more flexible than the shaft 12. The bending section 15 may be constructed, for example, using one of the conventional bending mechanisms described below, preferably with a relatively small bending radius (e.g., on the order of 1-2½ cm). Distal to the bending section 15 is a distal section 16 that is less flexible than the bending section 15. An ultrasound transducer 18 is housed within this distal section 16, preferably mounted transversely, and is used to obtain images (e.g., as described in application Ser. No. 10/996, 816).

In FIGS. 1A and 1B, bending section 15 includes a bending point 15a at the longitudinal center of the bending section 15, and the bending point 15a is located at a distance D1 from the longitudinal center of the transducer 18. Once the first probe 10 has been inserted in the patient's body (e.g., using an endoscope style control handle, not shown), the operator actuates a control mechanism (not shown, but located proximally to the flexible shaft 12) to bend the distal tip of the first probe 10 into a desired position. Since the bending section 15 is more flexible than the flexible shaft 12 or the distal section 16, the first probe 10 will bend at the bending section 15, centered at bending point 15a, in response to actuation of the bending control, as shown in FIG. 1B. As a result, the longitudinal center of the transducer 18 will be positioned out longitudinally at a distance D1 in a direction at least partly radial to the longitudinal axis of the flexible shaft 12.

FIGS. 1C and 1D illustrate a second probe 10' from the kit, which is identical to the probe of FIGS. 1A and 1B, except that the bending point 15a of the bending section 15 for the second probe 10' is located at a distance D2 from the transducer 18 instead of at a distance D1. Because the bending section 15 and bending point 15a are located in a location along the length of second probe 10' that is different than the locations of the bending section 15 and the bending point 15a in the first probe 10, when the operator actuates the bending controls (not shown), the second probe 10' will bend so that the longitudinal center of the transducer 18 is positioned out longitudinally at a distance D2 in a direction at least partly radial to the longitudinal axis of the flexible shaft 12, as shown in FIG. 1D.

By using a kit of probes, each having a bending section 15 and a bending point 15a that is located at different longitudinal distances from the transducer 18, the operator advantageously obtains the ability to position the transducer at the desired radial distance from the main shaft axis of the probe, to help obtain the desired image. The initial selection of which probe to use may be made using any medically appropriate technique, e.g., based on the size, weight, sex, or age of the patient, or any combination of such characteristics. Alternatively, a more precise estimate of the optimum radial distance maybe obtained using noninvasive imaging techniques such as CT, NMR, or conventional echocardiograms. Once an image of the relevant anatomy is obtained, the distance between the lower esophageal sphincter and the OPF may be determined from the image, and the appropriate probe may be selected from the kit based on that distance.

It is believed that one disadvantage of using a kit of probes is that the operator may select the wrong probe, in which case the operator will have to either proceed with a sub-optimum probe or withdraw the probe from the patient's body and then insert another probe to obtain the desired image. It is also believed that another disadvantage is that managing inventory for an entire kit of probes is more complicated than managing inventory for a single probe that can be used for most patients.

Figure 2B:
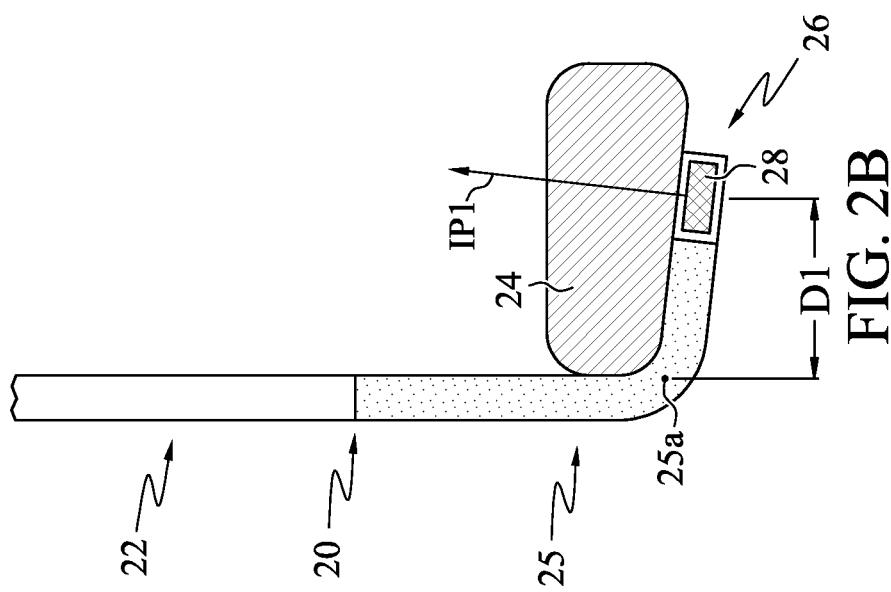
Figure 2A:
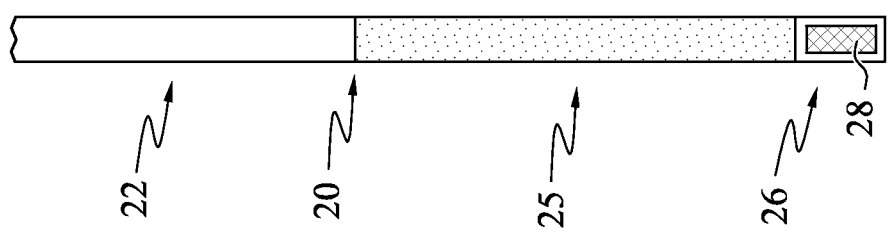

FIGS. 2A-2C illustrate an alternative probe 20 that avoids these possible disadvantages because it can be used for a much wider variety of patients than any individual probe from the above-described kit. The probe 20 has a flexible shaft 22 that is similar to the flexible shaft 12 described above. As in the FIG. 1 embodiment, the components that are proximal to the flexible shaft 22 and the mechanism for transmitting the operator's actuations of the controls to the working end of the probe are well know and are not described herein.

Distally beyond the flexible shaft 22 is a bending section 25 that is preferably more flexible than the shaft 22, with the proximal portions of the bending section 25 being more flexible than the distal portions of the bending section 25 (i.e., the elastic stiffness of the bending section 25 increases in the distal direction). Distal to the bending section 25 is a distal section 26 that is preferably less flexible than any portion of the bending section 25. An ultrasound transducer 28 is housed within this distal section 26, preferably mounted transversely as described above in connection with FIGS. 1A-1D.

As a result of the decreasing flexibility in the distal direction along the length of the bending section 25, when the bending control mechanism (not shown, but located proximally to the flexible shaft 22) is actuated by the operator, the bending section 25 will begin to flex about a point that is distal and adjacent to the anatomical constraint 24 (e.g., the lower esophageal sphincter). In the vertebra-based embodiments described herein, the vertebrae distal to the first unrestrained vertebra flex minimally or not at all initially, and then flex sequentially once all of the more proximal vertebrae have reached their limit of motion in a "domino" effect. Since the most proximal sections articulate before the more distal sections start to move, the more distal sections will remain in their initial unflexed position with respect to each other, as show in FIGS. 2B and 2C. Once the distal section contacts the mucosa of the stomach or esophagus, images can be obtained using any suitable imaging technique. If, based on the images, it turns out that the distal end is not positioned in the best location for imaging, the position of the probe may require adjustment to improve the images. If repositioning to a different LOD is desired, the probe can be unflexed, advanced further through the lower esophageal sphincter, then re-flexed to achieve a greater LOD (or conversely advanced less to achieve a shorter LOD).

For example, to obtain an ultrasound image of imaging plane IP1 shown in FIG. 2B (imaging plane IP1 is shown on edge, perpendicular to the page), the operator inserts the probe 20 through the mouth or nose into the esophagus until the longitudinal center of the transducer 28 extends a distance D1 past the relevant anatomical constraint 24 (i.e., the lower esophageal sphincter). The operator then actuates the control mechanism, which causes the bending section 25 of the probe 20 to bend at a bending point 25a. Because the more proximal portions of the bending section 25 are more flexible than the more distal portions of the bending section 25, the bending section 25 will bend relatively sharply at the lower left corner of the anatomically constraint 24 at the bending point 25a, and portions of the bending section 25 that are distal to the bending point 25a will remain relatively straight. Continued actuation of the bending control will cause the bending section 25 to bend further until the distal section 26 of the probe 20 comes in contact with the relevant anatomy (e.g., the superior portion of the fundus) as shown in FIG. 2B, with the transducer 28 positioned so that an image along imaging plane IP1 can be obtained.

Similarly, to obtain an ultrasound image on an imaging plane IP2 shown in FIG. 2C (imaging plane IP2 is shown on edge, perpendicular to the page), the operator inserts the probe 20 until the longitudinal center of the transducer 28 extends a distance D2 past the relevant anatomical constraint 24 and then actuates the control mechanism, which causes the bending section 25 of the probe 20 to bend relatively sharply at the lower left corner of the anatomically constraint 24 at a bending point 25b until the distal section 26 comes in contact with the relevant anatomy, with the transducer 28 positioned so that an image along imaging plane IP2 can be obtained.

A wide variety of mechanisms may be used to make the bending section 25 more flexible proximally and less flexible distally.

Figure 3C:
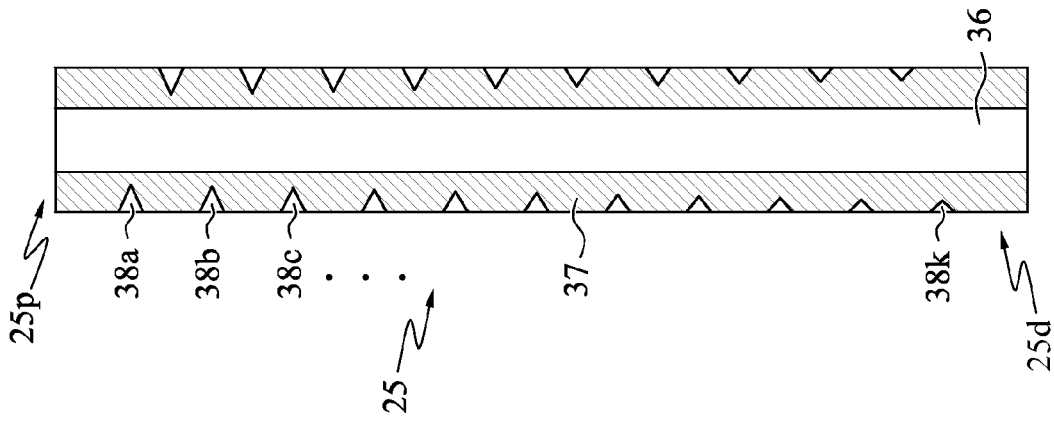
FIGS. 3A, 3B, and 3C show details of three alternative embodiments for the bending portion of the ultrasound probe of FIGS. 2A-2C.
Figure 3B:
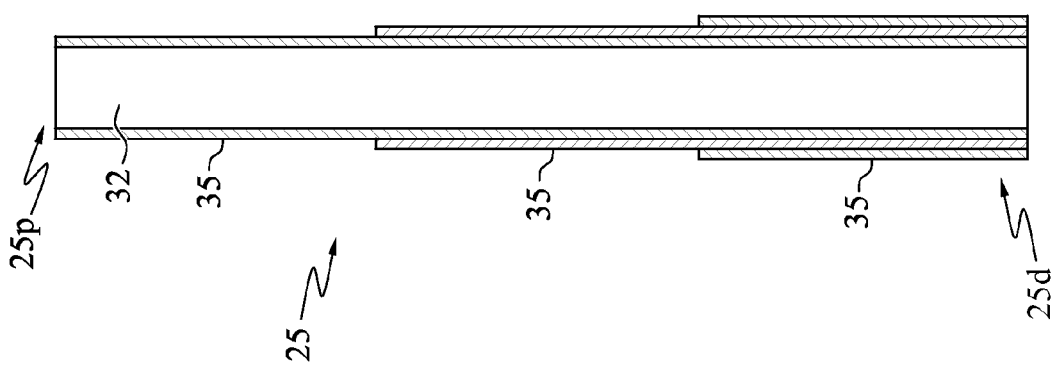
Figure 3A:
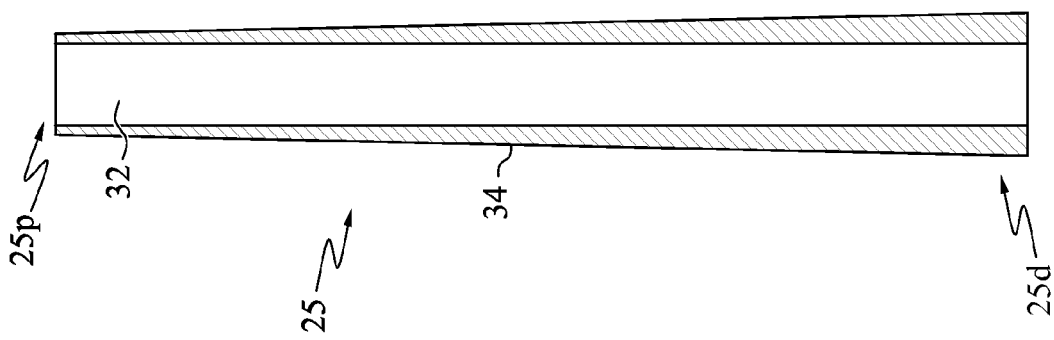

FIG. 3A illustrates a first example of a suitable multiflexibility bending section 25 with a proximal end 25p connecting to the flexible shaft 22 (not shown) and a distal end 25d connecting to the distal section 26 (not shown). This embodiment includes a central core 32 with a conventional bending mechanism such as a vertebrae/control wire construction that is commonly used in many medical devices (e.g., ultrasound probes, endoscopes, and catheters). The wires (not shown) to the transducer (not shown) pass through the central core 32. The central core may be configured, for example, as a vertebrae section (not shown) with a single or multiple pull wires (not shown) to affect the required motion. Suitable designs for the vertebra themselves include pinned, beaded, "wobble washer", and cut plastic extrusion designs. In all these designs, the vertebrae (not shown) are stacked and designed to provide the desired degree and radius of bending. Examples of suitable bending mechanisms include those disclosed in U.S. Pat. Nos. 5,271,382, 5,143,475, 5,271,381, 5,704,898, and 4,905,666, each of which is incorporated herein by reference in its entirety.

The central core 32 is surrounded by a jacket 34 (shown in cross section) with a thickness that gradually increases in the distal direction along the length of the jacket 34. In FIG. 3A, the thickness of the jacket 34 is exaggerated with respect to the central core 32 to make the change in thickness more visible. In practice, the jacket 34 is preferably much thinner than shown in FIG. 3A. Suitable materials for the jacket 34 include elastomerics and thermoplastics such as C-flex, Kraton, silicone, polyurethane, natural rubber, synthetic rubber, etc. In one preferred embodiment, the thickness of the jacket 34 varies between about 0.1 mm and about ¼ mm at the proximal end 25p, and increases gradually so that the thickness at the distal end 25d is about three or four times the thickness at the proximal end 25p.

In an alternative embodiment (not shown) to the embodiment illustrated in FIG. 3A, a central core similar to the central core 32 illustrated in FIG. 3A is surrounded by a jacket with a constant thickness along the length of the alternative central core. However, instead of decreasing the flexibility of the jacket in the distal direction by increasing the thickness of the jacket in the distal direction, the flexibility is decreased in the distal direction by increasing the durometer of the jacket material in the distal direction. This may be implemented, for example, by using a curable material such as polyurethane or silicone and curing the material of the jacket to different degrees at different points along the length of the jacket (e.g., by using heat or ultraviolet light curing or variable catalysts).

FIG. 3B illustrates another example of a multi-flexibility bending section. However, instead of gradually decreasing the flexibility of the jacket in the distal direction by gradually increasing the thickness of the jacket in the distal direction, the flexibility of the bending section 25 is decreased in the distal direction in a stepwise manner. This embodiment uses a central core 32 similar to the core describe above in connection with the FIG. 3A embodiment. The central core 32 is preferably completely surrounded by a first jacket layer 35A (shown in cross section). The distal-most two-thirds of the bending section 25 is then surrounded by a second jacket layer 35B, and the distal-most one-third of the bending section 25 is then surrounded by a third jacket layer 35C. Note that while FIG. 3B illustrates three steps with each of the jacket layers 35A, 35B, and 35C, the number of steps can be varied to provide the desired bending characteristics. The same materials used for the jacket 34 in the FIG. 3A embodiment may be used in this embodiment, and a similar central core 32 may also be used. A suitable thickness for each of the jacket layers 35A, 35B, and 35C is between about 0.1 and about 0.25 mm. Note that the thicknesses of the jacket layers 35A, 35B, and 35C are exaggerated in FIG. 3B with respect to the central core 32 to make the change in thickness more visible.

FIG. 3C illustrates yet another example of a multi-flexibility bending section. In this embodiment, a wall 37 that is preferably cylindrical or elliptical surrounds a central channel 36. The wires (not shown) to the transducer (note shown) pass through this central channel 36. A suitable wall thickness is between about ¼ mm and about 1 mm, and suitable materials for the wall 37 include polyurethane, nylon, polyethylene, Pebax, plus other polymers and copolymers known to those skilled in the art. Notches 38 are cut into the wall 37 at intervals along the length of the wall 37. One suitable pattern for the notches is illustrated in FIG. 3C, with the notches 38 on one cross-sectional side of the wall 37 (on the right side of FIG. 3C) staggered along the length of the wall 37 from the notches 38 on the other side of the wall 37 (on the left side of FIG. 3C). This results in a plurality of vertebra-like sections that are separated by the notches 38. The notches at the proximal end 25p of the bending section 25 are also wider and/or deeper than the notches at the distal end 25d, so that the proximal end 25p will be more flexible than the distal end 25d. One suitable range of notch 38 sizes would range from about half the thickness of wall 37 at the proximal end 25p up to the full thickness of wall 37 at the distal end 25d, and other notch configurations that provide the desired flexibility gradient will be apparent to persons skilled in the relevant arts. Optionally, the notches 38 may be filled with a suitable material that does not impede bending (e.g., silicone) and/or the walls 37 may be surrounded by a thin sheath (not shown) of, e.g., C-flex, Kraton, silicone, etc.

In one variation of this embodiment (not shown), instead of alternating the notches on the opposing sides of the wall 37 illustrated in FIG. 3C, annular notches may be used that are deeper and or wider at the proximal end 25p than at the distal end 25d. Alternatively, constant-sized notches may be used, but the pitch of the constant-sized notches can be varied, i.e., from constant-sized notches that are spaced relatively close together at the proximal end 25p to a more distant spacing at the distal end 25d. In another variation of this embodiment (not shown), the alternating notches may be replaced by a helical notch that runs circumferentially around and along the length of the entire bending section 25, with the width and/or depth of the helical notch decreasing as the helical notch approaches the distal end 25d of the bending section 25. Alternatively, instead of varying the width and/or depth of the helical notch, a helical notch with a constant width and depth may be used, but the helical pitch of the helical notch is varied, i.e., from a relatively tight helix at the proximal end 25p to a relatively looser helix at the distal end 25d. In yet another alternative embodiment (not shown), vertical notches that run along the longitudinal length of the bending section 25 maybe cut into the walls 37, with the width and/or depth of the vertical notches gradually decreasing distally from the proximal end 25p to the distal end 25d of the bending section 25.

In other alternative embodiments (not shown), instead of relying on the jacket or walls to vary the flexibility of the bending section 25, the changes in flexibility may be designed into the central core 32 by, e.g., varying the dimensions of the individual segments contained within the central core 32 to provide more flexibility at the proximal end 25p and less flexibility at the distal end 25d, in a manner that will be apparent to persons skilled in the relevant arts. When the bending section 25 includes a braid, variations in flexibility may also be provided in the braid by, e.g., painting a triangular pattern of flexible paint into the braid, or by impregnating sequential sections of the braid with different materials. Numerous other alternative ways to make the bending section 25 more flexible proximally and less flexible distally will also be apparent to persons skilled in the relevant arts.

In yet another preferred embodiment, the bending section can provide controllable movement and steering of the probe while maintaining a variable stiffness along the longitudinal length of the bending section. This is accomplished with a bending section that has a sheath enclosing a series of axially-arranged vertebrae aligned end to end along the longitudinal length of the bending section. Extending through the spine formed by the vertebrae are a series of spring plates that together have a varying stiffness along the length of the spine, with increasing stiffness towards the distal end of the bending section where the spring plates have a greater stiffness.

Figure 5A:
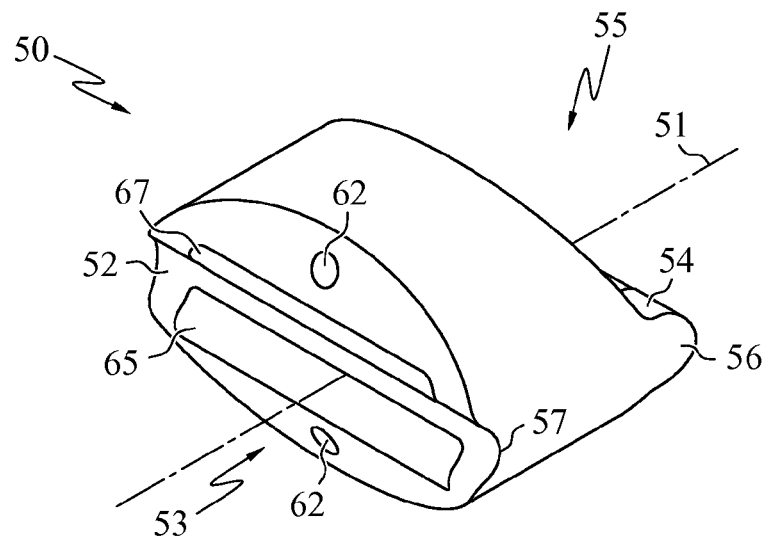
FIGS. 5A, 5B, and 5C show isometric, end, and cross-sectional views of a vertebra of a fourth alternative preferred embodiment of the bending portion of the probe of FIG. 2A.
Figure 5B:
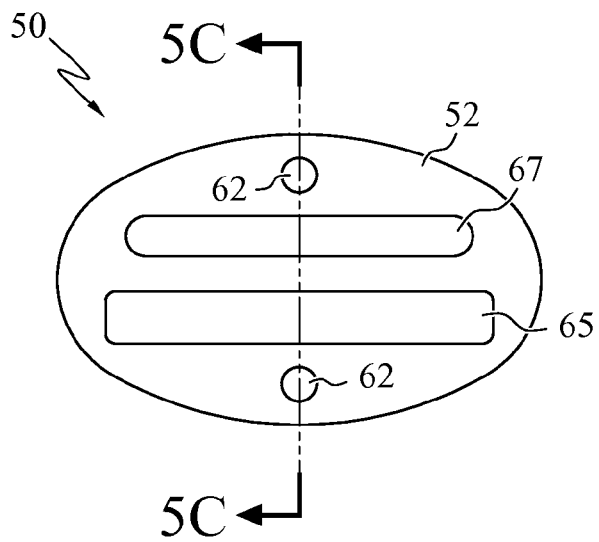
Figure 5C:
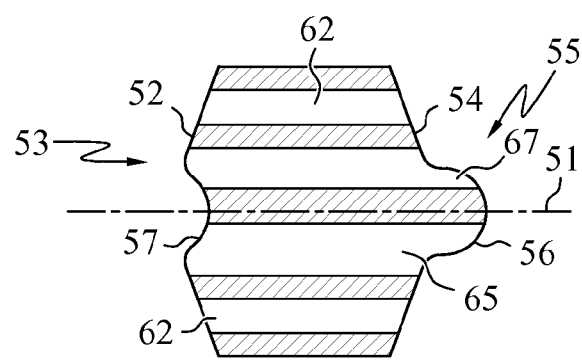
Figure 6:
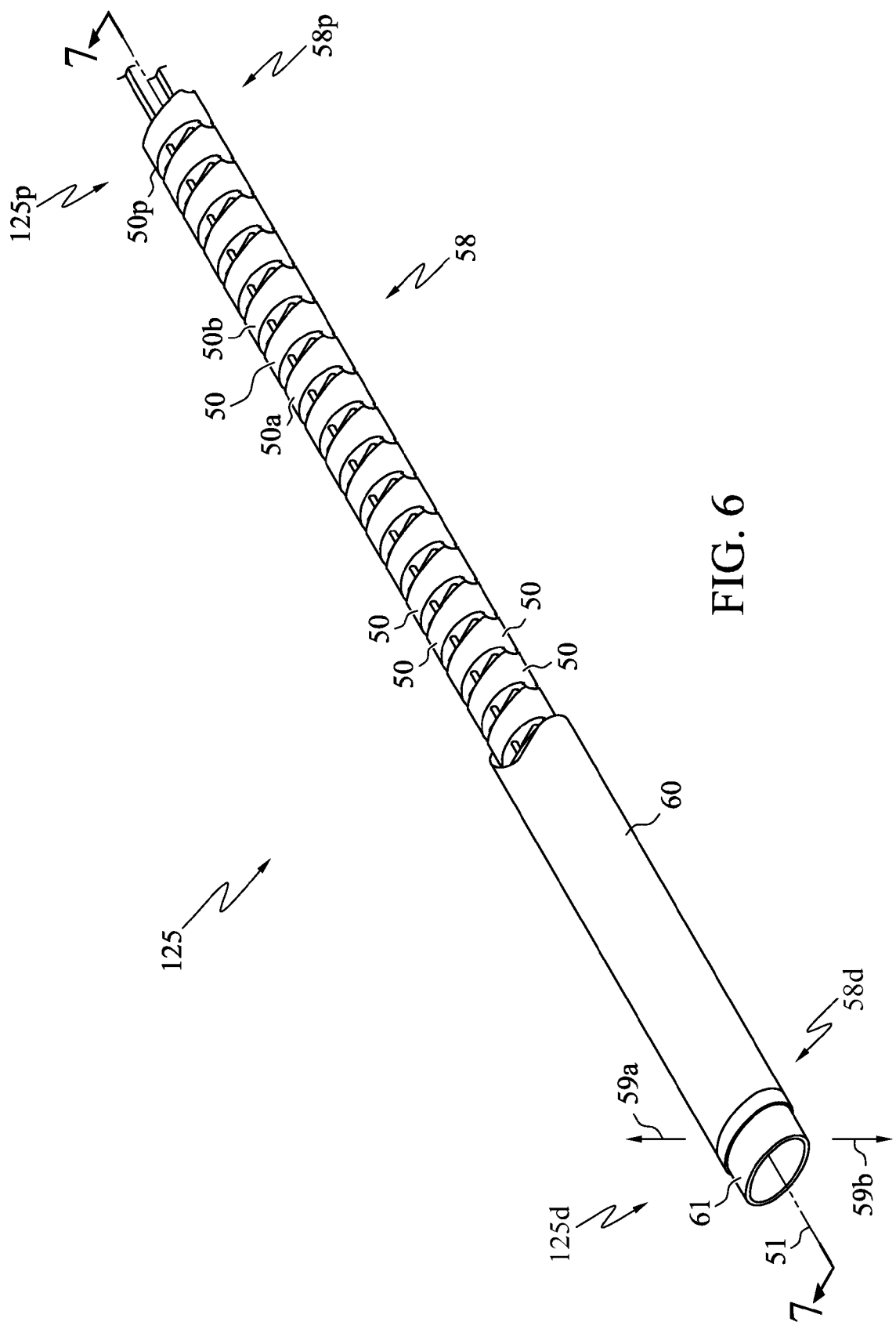
FIG. 6 shows an isometric view of the fourth alternative preferred embodiment of the bending portion of the probe of FIG. 2A.

FIGS. 5A-5C illustrate a vertebra 50 having a body with a longitudinal axis 51 and an oval cross-section in a plane orthogonal to the axis 51. Vertebra 50 also has a proximal face 52 at a proximal end 53, and a distal face 54 at a distal end 55. The distal end 55 has a protrusion 56 and the proximal end 53 has a groove 57. The protrusion 56 and groove 57 are formed to mate or interface with, respectively, a corresponding groove 57a and protrusion 56b of adjacent identically-formed vertebrae 50a and 50b disposed, respectively, distally and proximally of the vertebra 50, as illustrated in FIG. 6. When assembled along the same longitudinal axis 51 into a spine 58 having a proximal end 58p and a distal end 58d, as illustrated in FIG. 6, the interfacing protrusions and grooves of adjacent vertebrae slide against each other, and the engagement between the interfacing protrusions 56 and grooves 57 directs the sliding movement of the vertebra 50 proximate the distal end 58d in radial directions 59a and 59b. As illustrated in FIG. 6, the spine 58 is covered by a sheath 60 (shown in part) to form a bending section 125 having a proximal end 125p with a proximal end vertebra 50p, and having a distal end 125d with a distal connector 61. The proximal end 125p of the bending section 125, at proximal end vertebra 50p, engages the distal portion of a flexible shaft (not shown) similar to the flexible shaft 22 illustrated in FIG. 2A. In a similar manner, the distal end 125d of the bending section 125, at the distal connector 61, engages the proximal portion of a distal section (not shown) similar to the distal section 26 illustrated in FIG. 2A. The vertebrae 50 and distal connector 61 can be made of any hard plastic (eg polycarbonate, ABS, etc.). The sheath 60 is preferably made from an elastomeric biocompatible material such as kraton, polyurethane, silicone, etc. The sheath 60 fits over the vertebrae 50 so as to hold each vertebrae 50 adjacent to each other and to maintain a unified spine 58 structure. The use of the sheath 60 simplifies the manufacture of the spine 58 because each adjacent vertebrae 50 can be assembled next to each other and held in position without the use of a direct connection between each adjacent vertebrae 50, by using the sheath 60 to prove a enveloping structure connecting the vertebrae 50 together to form the spine 58. Alternatively, the sheath 40 can be a shrink wrap that is disposed around spine 58, and shrunk to hold the vertebrae 50 together in spine 58.

As illustrated in FIGS. 5A-5C and 7, two channels 62 are formed within each vertebra 50 that extend longitudinally along the entire length of the bending section 125 (when the vertebrae are aligned to form the bending section 125) until reaching the distal connector 61 where the channels 62 merge into a single channel 63 extending through the distal connector 61. Each of the channels 62 guide a wire 64 that slidably extends through the bending section 125 to connect the proximal end of the probe (not shown) to the distal end of the probe (not shown). The wires 64 are moved at the proximal end of the probe in the direction of the longitudinal axis 51 to cause the bending section 125 to move in either of the two radial directions 59a or 59b. The wires 64 may be made of any material with a suitably high tensile strength and low stretch, (e.g., plastic, or metal such as stainless steel). Also formed in each vertebra 50 is a channel 67 extending through the spine 58 to guide the wiring connecting the ultrasound transducer 28 distal of the spine 58 to ultrasound equipment proximal to the spine 58, and it most preferably a ribbon cable such as that disclosed in U.S. Provisional Patent Application No. 60/743, 702, filed Mar. 23, 2006, which is incorporated by reference in its entirety.

As also illustrated in FIGS. 5A-5C and 7, a channel 65 extends longitudinally through each vertebra 50 along the entire length of the bending section 125 (when the vertebrae are aligned to form the bending section 125) until reaching the distal connector 61 where the channel 65 merges into the single channel 63. The channel 65 preferably has a rectangular cross-sectional shape guiding one or more spring plates 66 through most of the longitudinal length of the bending section 125. The spring plates 66 are preferably made of a material with a high elastic limit such as spring steel (e.g. stainless steel spring steel). The spring plates 66 are also preferably formed to naturally retain a longitudinally straight form, and with a stiffness that provides a resistance to bending forces. Also, when assembling the spine 58, the spring plates 66 provide a structure onto which each vertebrae can be installed by sliding each vertebra 50 over an end of the spring plates 66 until forming the completed assembly of the spine 58 and, after all the vertebrae are in place, the spine assembly can be covered and held together by the sheath 60.

Figure 7:
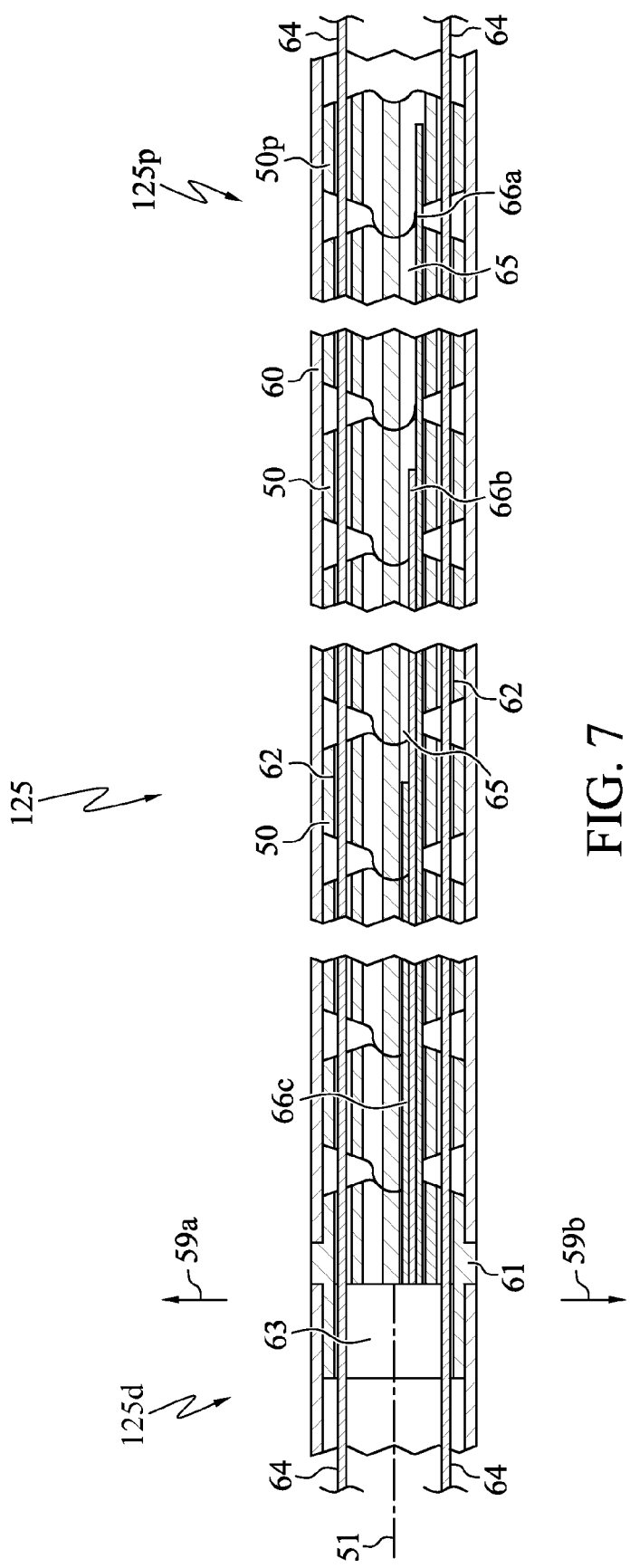
FIG. 7 shows a cross-sectional view of the bending portion of FIG. 6.
Figure 8:
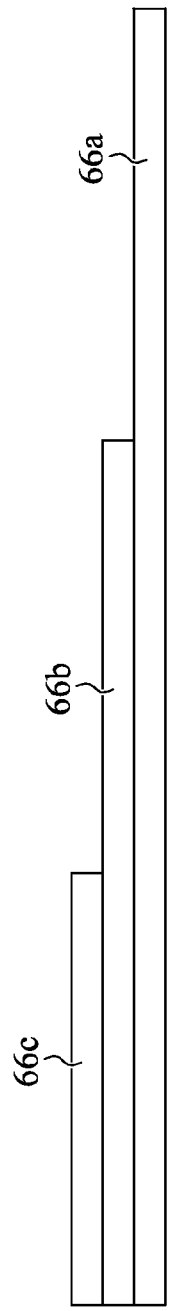
FIG. 8 shows the spring plate of FIG. 7.

As illustrated in FIGS. 7 and 8, a first spring plate 66a is disposed within the channel 65 and extends from the proximal end vertebra 50p to the distal connector 61. The first spring plate 66a is slidably disposed within the channel 65 extending through the vertebrae 50 and fixedly connected to the distal connector 61 at the channel 65 extending through the distal connector 61. A shorter second spring plate 66b is disposed adjacent and parallel to the first spring plate 66a. Similar to the first spring plate 66a, the second spring plate 66b is slidably disposed within the channel 65 extending through the vertebrae 50 and fixedly connected to the distal connector 61 at the channel 65 extending through the distal connector 61. A third spring plate 66c, shorter than the second spring plate 66b, is disposed adjacent and parallel to the second spring plate 66b. Similar to the first and second spring plates 66a and 66b, the third spring plate 66c is slidably disposed within the channel 65 extending through the vertebrae 50 and fixedly connected to the distal connector 61 at the channel 65 extending through the distal connector 61.

As can be appreciated in the design illustrated in FIG. 7, when the wires 64 are moved, and the bending section 125 is caused to move in the directions of radial directions 59a or 59b, the spring plates 66a, 66b, and 66c slide relative to each other within the channel 65 while remaining fixed at the distal connector 61. As can also be appreciated, the radial-directed movement of the bending section 125 is resisted by one or more of the spring plates 66, and there is thus no need for a radially reinforced or braided jacket surrounding the spine to provide stiffness to the spine or resistance to the bending forces as seen with other designs. The radial-directed movement of the vertebrae 50 disposed around only the first spring plate 66a, near the proximal end 125p of the bending section 125, is resisted by the stiffness of the first spring plate 66a. The radial-directed movement of the vertebrae 50 disposed around the first and second spring plates 66a and 66b is resisted by the combined stiffness of the first and second spring plates 66a and 66b. The radial-directed movement of the vertebrae 50 disposed around the first, second and third spring plates 66a-66c is resisted by the combined stiffness of the first, second and third spring plates 66a-66c. As can be appreciated, the combined stiffness of the first and second spring plates 66a and 66b is greater than the stiffness of the first spring plate 66a, and the combined stiffness of the first, second and third spring plates 66a-66c is greater than the stiffness of the first spring plate 66a or the combination of the first and second spring plates 66a and 66b. By this arrangement of the spring plates 66, the stiffness of the bending section 125 increased in the distal direction along the longitudinal length of the bending section 125.

Alternatively, instead of adjacent spring plates 66 providing a variable stiffness or flexibility to the bending section 125, a single spring plate can be used that has material properties that provide a varying stiffness along the length of the spring plate, such as a combination of two or more materials where a stiffer material of the combination dominates the combination in the stiffer portions of the spring plate. In another alternative, the adjacent spring plates 66 can be replaced with a single spring plate that has a thickness that varies along the length of the spring plate, with the varying thickness providing a variable stiffness to the spring plate. In yet another alternative, the adjacent spring plates 66 can be replace by one or more spring plates that have shapes that provide a variable stiffness, such as a single spring plate that has a constant thickness along its length but tapers in its width to have a narrower cross-sectional width that reduces stiffness of the spring plate, or a constant width and stepwise or gradual variations in thickness. In still another alternative, the adjacent spring plates 66 can be replaced with one or more spring plates that are structurally modified to provide a variable stiffness along the length of the spring plate, such as by constructing the spring plate to have one or more predetermined holes or notches in or through the surface of the spring plate to vary the stiffness of the spring plate along its length. In alternative embodiments (not shown), alternative stiffening members (e.g., one or more metal or plastic rods or bars) may be used in place of the illustrated spring plates.

Figure 4B:
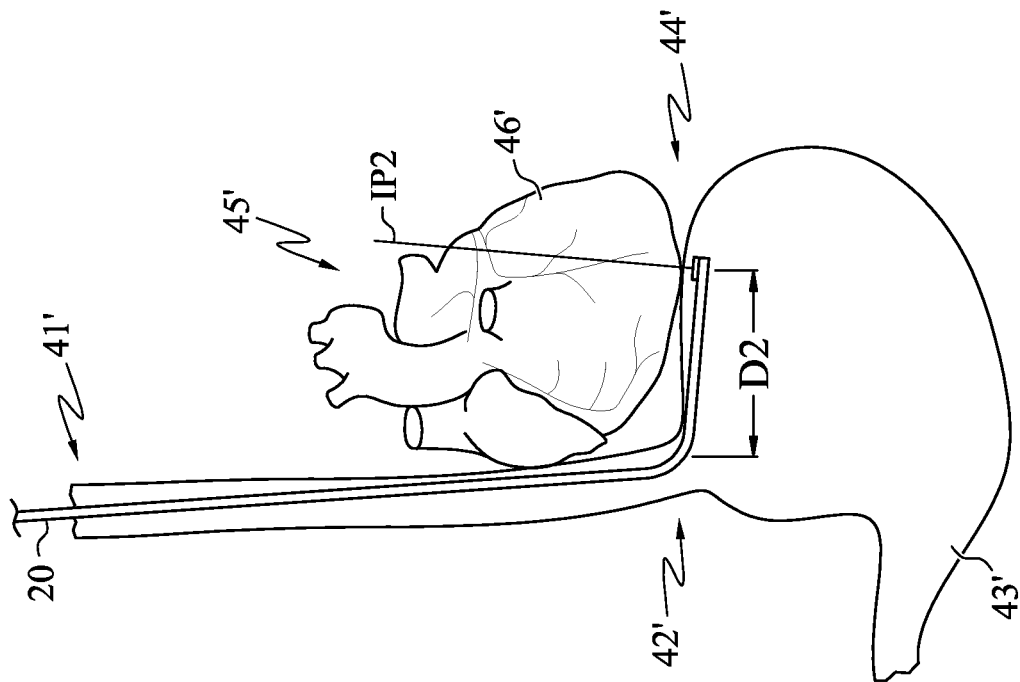
FIGS. 4A and 4B show the distal portion of the ultrasound probe of FIGS. 2A-2C being used in subjects with different sized anatomies.
Figure 4A:
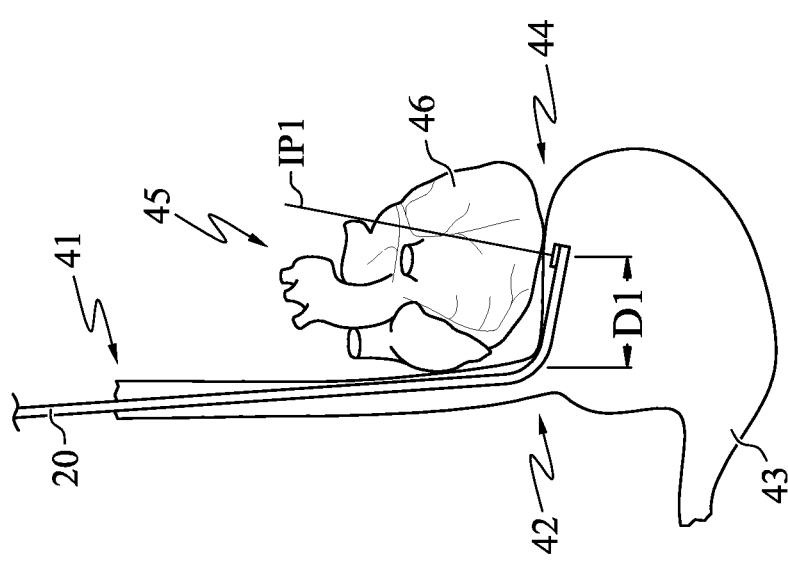

Varying the flexibility of the bending section 25 in the proximal to distal direction as described above makes a single probe fit a wide variety of anatomies, despite the fact that the LOD may vary dramatically from patient to patient. FIG. 4A illustrates the relevant anatomic structures for an average size person, including the esophagus 41, the lower esophageal sphincter 42, the stomach 43, the fundus 44, the heart 45, and the left ventricle 46; and FIG. 4B illustrates the corresponding structures in a larger person (labeled with corresponding reference numbers 41'-46'). Although the LOD for the smaller person is D1, and the LOD for the larger person is D2, in both cases the distal end 26 of the probe 20 can be easily positioned at the OPF, where the probe can be used to acquire images of the desired imaging planes IP1 and IP2, respectively.

If the flexibility of the interface between the bending section and the shaft is greater than the flexibility of the proximal portion of the bending section, it can sometimes be difficult to manipulate the distal section (which houses the transducer) into position. This difficulty arises because attempts to advance the distal section by pushing on the shaft may cause the interface between the shaft and bending section to bend or buckle instead of the desired advancing motion. To avoid this difficulty, it is preferable to design the interface to have either the same flexibility as the proximal portion of the bending section or less flexibility than the proximal portion of the bending section.

Figure 9:
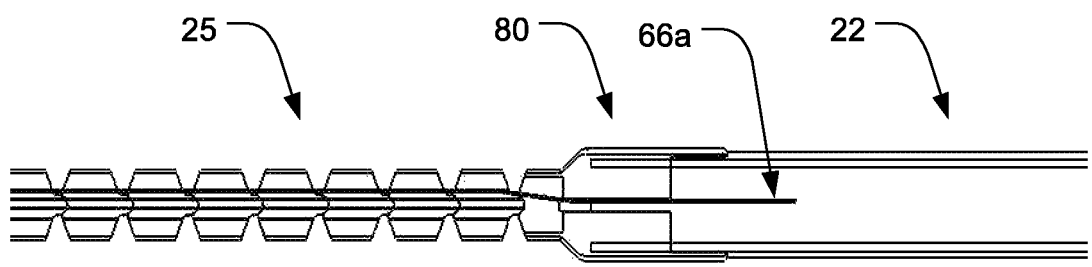
FIG. 9 shows a detail of the interface between the shaft and the bending portion.

In embodiments that use spring plates (such as the spring plates 66 depicted in FIGS. 7 and 8), one way to accomplish this is by extending the most proximal spring plate 66a out of the bending section 25 in a proximal direction and into the shaft section 22, as depicted in FIG. 9. In these embodiments, the distal end of the shaft section would preferably include a channel dimensioned to accept the proximal end of the spring plate (e.g., with dimensions similar to the channel 65 depicted in FIGS. 5A-5C). Preferably, this channel should be dimensioned so as to permit sliding of the spring plate within the channel, and the spring plate should extend far enough into this channel to provide the desired flexibility characteristics at the interface. Of course, persons skilled in the relevant arts will appreciate that a variety of other techniques may be used to provide the desired flexibility characteristics at the interface 80 between the shaft and the bending section. Examples include, but are not limited to: making the elastomeric cover section preferentially stiffer in order to lessen the transition of stiffness between the shaft and the bending section; using a vertebra or series of vertebrae designed to limited the range of motion at the first juncture between the shaft and the bending section; adding a spring section that is externally deployed at the juncture to limit the range of motion and/or to effect a change of stiffness; etc.

Note that for TEE imaging of the TGSAV, a relatively sharp bend is anatomically appropriate because the esophagus 41 is relatively straight and the stomach cavity is large, and a sharp bend facilitates improved contact with the superior portion of the fundus 44. This stands in contrast to conventional ultrasound probes, endoscopes, and catheters that have traditionally been designed with bending mechanisms designed to bend smoothly and gradually, so as to provide easier their passage through the various lumens and cavities of the body.

While the multi-flexibility bending section is described above in the context of thin TEE probes, it can also be used with conventional ½ inch diameter TEE probes, to make it easier to position the probe at the OPF. Moreover, while the various embodiments are described above in the context of TEE and obtaining images of the TGSAV of the heart, the probes may also be used to obtain other transesophageal images, and may even be used in cavities other than the esophagus, outside of the body when access is limited, or in non-medical applications. The multi-flexibility bending section may also be incorporated into probes, endoscopes, or catheters in non-ultrasound medical applications, and may even be used in non-medical uses where similar bending characteristics are desirable. Numerous other modifications to the above-described embodiments will be apparent to persons skilled in the relevant arts, and are also included within the purview of the invention. For example, instead of an ultrasound transducer 28, the multi-flexibility bending section can be used with an optical probe, with a sensor that is acoustic, electrical, or magnetic, or with a device that emits or detects radiation or vibrations.

Optionally, a medical grade lubricant (e.g., silicone oil) may be applied to the outside of the shaft in any of the above-describe embodiments to provide lubricity, inhibit moisture intrusion, as well as other benefits, particularly in situations when the shaft is left in position for a long time.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

I claim:

1. A probe, comprising:
   a shaft;
   a distal section having a sensor;
   a bending section disposed between the shaft and the distal section, the bending section having a proximal portion and a distal portion, wherein the distal portion is flexible, the proximal portion is more flexible than the distal portion, and the flexibility of the proximal portion of the bending section is greater than or equal to the flexibility of an interface between the bending section and the shaft, and wherein the bending section comprises a plurality of axially-arranged vertebrae; and
   a bending mechanism configured to bend the bending section when actuated,
   wherein the bending section is configured such that when a part of the bending section is distal to a constraint that prevents bending and the bending mechanism is actuated, a proximal section of the part articulates before more distal sections of the part articulate, resulting in a bend in the bending section, wherein the axial location of the bend with respect to the bending section depends on where the bending section is positioned with respect to the constraint.

2. The probe of claim 1, wherein the sensor comprises at least one of an optical sensor, a thermal sensor, an imaging device, and a pressure sensor.

3. The probe of claim 2, wherein the bending mechanism comprises at least one pull wire.

4. The probe of claim 1, wherein the flexibility of the bending section decreases gradually in the proximal to distal direction.

5. The probe of claim 1, wherein the flexibility of the bending section decreases in a stepwise manner in the proximal to distal direction.

6. The probe of claim 1, wherein the bending section contains a middle portion disposed between the proximal portion and the distal portion, wherein the proximal portion is more flexible than the middle portion and the middle portion is more flexible than the distal portion.

7. The probe of claim 6, wherein the sensor comprises at least one of an optical sensor, a thermal sensor, an imaging device, and a pressure sensor.

8. The probe of claim 7, wherein the bending mechanism comprises at least one pull wire.

9. The probe of claim 1, wherein the sensor comprises an ultrasound transducer.

10. The probe of claim 9, wherein the bending mechanism comprises at least one pull wire.

11. The probe of claim 9, wherein the flexibility of the bending section decreases gradually in the proximal to distal direction.

12. The probe of claim 9, wherein the flexibility of the bending section decreases in a stepwise manner in the proximal to distal direction.

13. The probe of claim 9, wherein the bending section contains a middle portion disposed between the proximal portion and the distal portion, wherein the proximal portion is more flexible than the middle portion and the middle portion is more flexible than the distal portion.

14. The probe of claim 13, wherein the bending mechanism comprises at least one pull wire.

\* \* \* \* \*